(12) United States Patent
Wall, Jr. et al.

(10) Patent No.: US 11,020,523 B2
(45) Date of Patent: Jun. 1, 2021

(54) CANISTER STAND

(71) Applicants: Simeon Wall, Jr., Shreveport, LA (US); Daniel A. Del Vecchio, Boston, MA (US)

(72) Inventors: Simeon Wall, Jr., Shreveport, LA (US); Daniel A. Del Vecchio, Boston, MA (US)

(73) Assignee: Surgistem Technologies LLC, Boston, MA (US)

( * ) Notice: Subject to any disclaimer, the term of this patent is extended or adjusted under 35 U.S.C. 154(b) by 0 days.

(21) Appl. No.: 16/240,980

(22) Filed: Jan. 7, 2019

(65) Prior Publication Data

US 2019/0167891 A1    Jun. 6, 2019

Related U.S. Application Data

(62) Division of application No. 14/870,294, filed on Sep. 30, 2015, now Pat. No. 10,173,000.

(51) Int. Cl.
| | | |
|---|---|---|
| *F16M 11/00* | (2006.01) | |
| *A61M 5/142* | (2006.01) | |
| *A61M 1/00* | (2006.01) | |
| *A61M 3/02* | (2006.01) | |

(52) U.S. Cl.
CPC ...... *A61M 5/14212* (2013.01); *A61M 1/0058* (2013.01); *A61M 3/0275* (2013.01); *A61M 3/0283* (2013.01); *A61M 2209/084* (2013.01)

(58) Field of Classification Search
CPC ... A61J 1/14; A61J 1/16; F16M 11/00; A61M 1/0209; A61M 1/00; A61M 39/00; A47B 73/002; A77B 73/18
USPC ............... 604/542, 319; 417/361; 312/351.3; 248/682
See application file for complete search history.

(56) References Cited

U.S. PATENT DOCUMENTS

| | | | |
|---|---|---|---|
| 4,815,462 A | 3/1989 | Clark | |
| 5,002,538 A | 3/1991 | Johnson | |
| 6,258,054 B1 | 7/2001 | Mozsary et al. | |
| 6,638,238 B1 | 10/2003 | Weber et al. | |
| 6,942,677 B2 | 9/2005 | Nita et al. | |
| 6,979,328 B2 * | 12/2005 | Baerveldt | A61F 9/00781 606/41 |
| 8,100,874 B1 * | 1/2012 | Jordan | C12M 47/04 604/319 |
| 9,636,134 B2 | 5/2017 | Werner | |
| 2005/0261670 A1 | 11/2005 | Weber et al. | |
| 2006/0224144 A1 | 10/2006 | Lee | |
| 2010/0152614 A1 | 6/2010 | Mark | |

* cited by examiner

*Primary Examiner* — Deanna K Hall
(74) *Attorney, Agent, or Firm* — R. Keith Harrison

(57) ABSTRACT

A canister stand suitable for holding at least one dispensing canister in a system for removal, delivery and/or transplantation of body tissues and other substances in medical procedures may include a canister stand frame. A frame panel may be carried by the canister stand frame. At least one overhang may be formed by the canister stand frame. At least one canister opening may be provided in the frame panel at the at least one overhang. The at least one canister opening may be suitably sized and configured to accommodate the at least one dispensing canister.

20 Claims, 10 Drawing Sheets

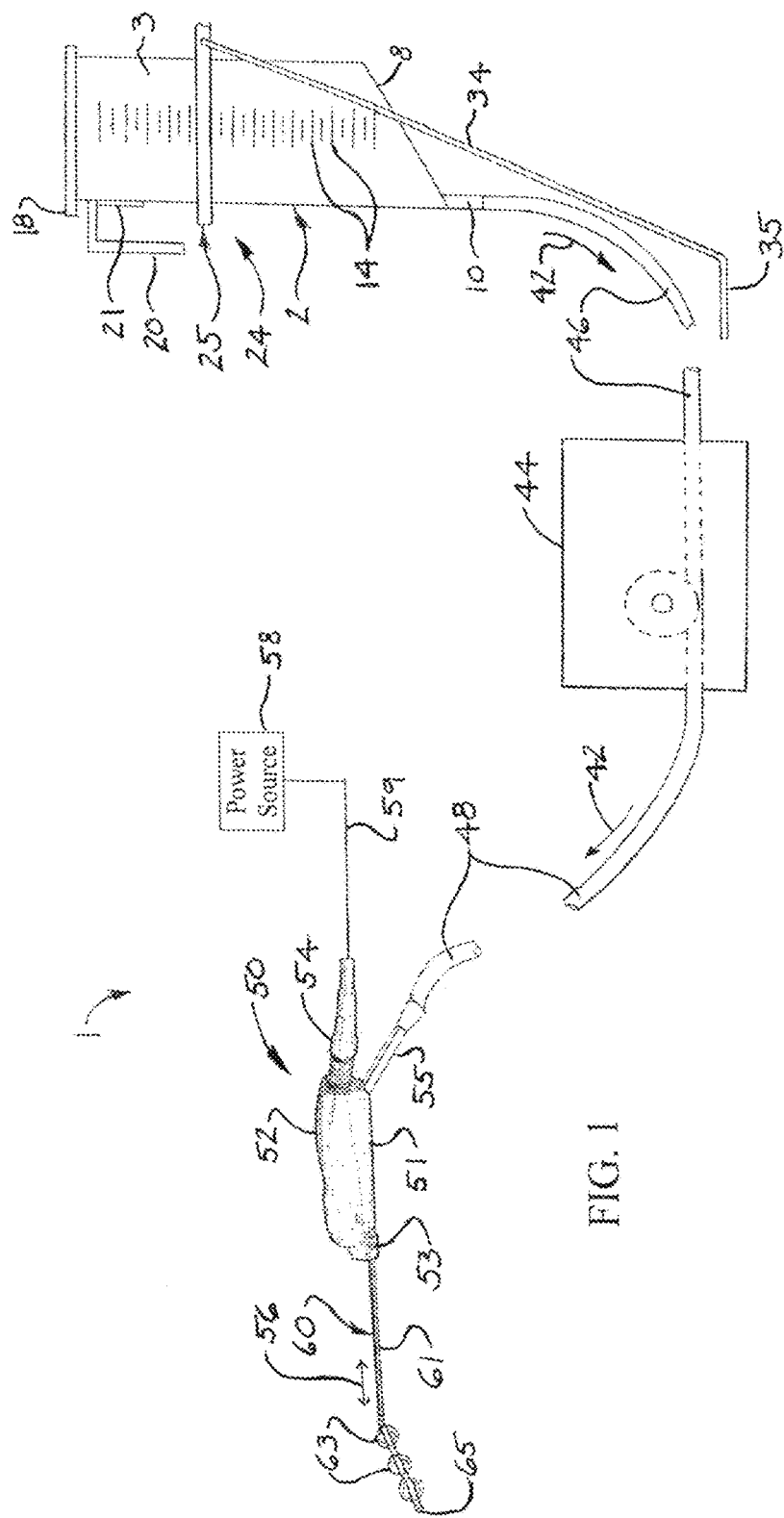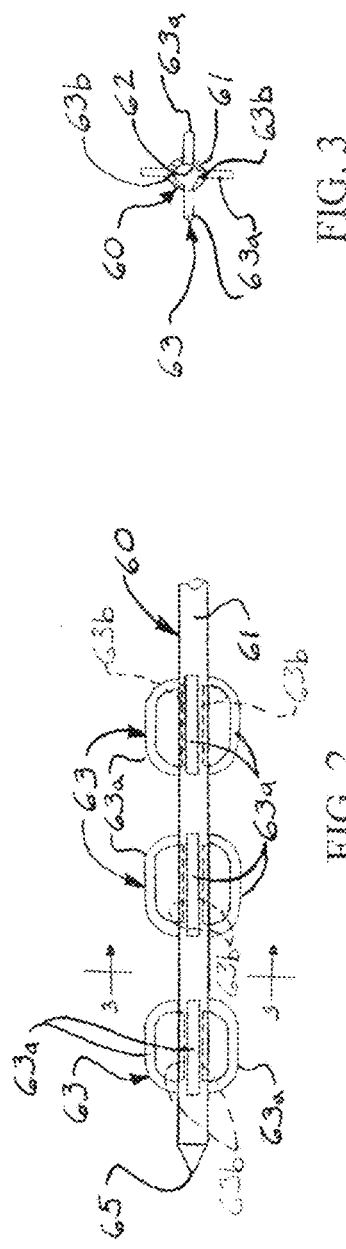
FIG. 1
FIG. 2
FIG. 3

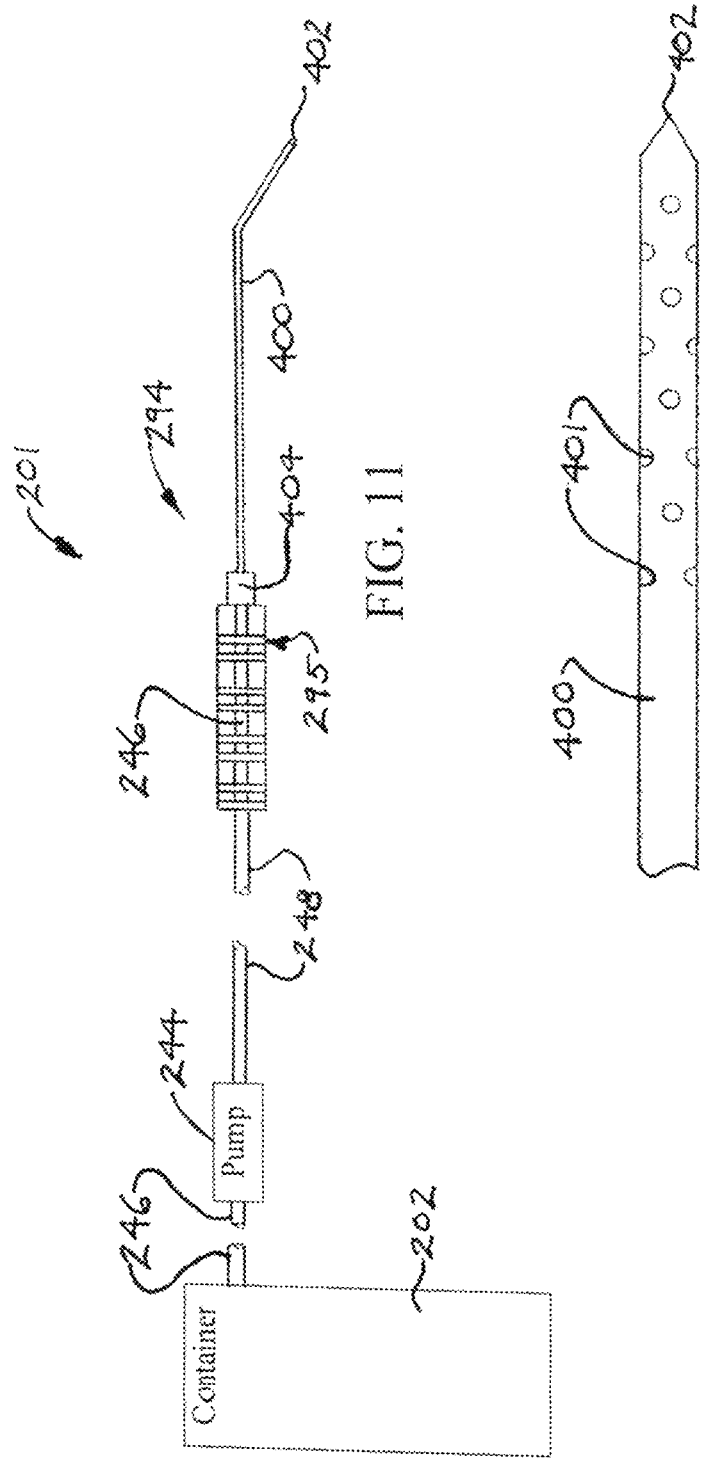

CANISTER STAND

CROSS-REFERENCE TO RELATED APPLICATIONS

This is a divisional of application Ser. No. 14/870,294, filed Sep. 30, 2015 and entitled SYSTEMS, APPARATUSES AND METHODS FOR TISSUE AND SUBSTANCE REMOVAL, DELIVERY AND/OR TRANSPLANTATION, which claims the benefit of U.S. provisional application No. 62/058,295, filed Oct. 1, 2014 and entitled SYSTEMS, APPARATUSES AND METHODS FOR TISSUE REMOVAL, DELIVERY AND/OR TRANSPLANTATION, each of which applications is hereby incorporated by reference herein in its entirety.

FIELD

Illustrative embodiments of the disclosure generally relate to systems, apparatuses and methods for removal, delivery and/or transplantation of body tissues and other substances in medical procedures. More particularly, illustrative embodiments of the disclosure relate to systems, apparatuses and methods for removal, delivery and/or transplantation of body tissues and other substances such as adipose tissue, preparation fluids, or filler materials for tissue rejuvenation, body shaping or other medical purposes.

BACKGROUND

The background description provided herein is solely for the purpose of generally presenting the context of the illustrative embodiments of the disclosure. Aspects of the background description are neither expressly nor impliedly admitted as prior art against the claimed subject matter.

Skin, adipose, musculoskeletal, and other body tissues may change in appearance and/or lose function with age and/or use due to injury, disease, wear, aging and/or other causes. One of the goals of plastic surgical procedures may include removal, delivery and/or transplantation of natural or man-made substances and body tissues in rejuvenation or shaping of the tissues to improve or restore the original appearance and/or function of the tissues. For example, conventional tissue shaping procedures may include liposuction, whereas tissue rejuvenation procedures may include the use of filler materials or adipose stem/progenitor cells to augment areas or promote angiogenesis and adipose/collagen tissue regeneration. However, such procedures may have less-than-optimum results and scarring.

Accordingly, systems, apparatuses and methods for removal, delivery and/or transplantation of substances or body tissues such as adipose tissue for tissue rejuvenation, body shaping or other medical purposes are needed.

SUMMARY

Illustrative embodiments of the disclosure are generally directed to a canister stand suitable for holding at least one dispensing canister in a system for removal, delivery and/or transplantation of body tissues and other substances in medical procedures. An illustrative embodiment of the canister stand may include a canister stand frame. A frame panel may be carried by the canister stand frame. At least one overhang may be formed by the canister stand frame. At least one canister opening may be provided in the frame panel at the at least one overhang. The at least one canister opening may be suitably sized and configured to accommodate the at least one dispensing canister.

BRIEF DESCRIPTION OF THE DRAWINGS

Illustrative embodiments of the disclosure will now be described, by way of example, with reference to the accompanying drawings, in which:

FIG. 1 is a diagram of an illustrative embodiment of the systems for tissue removal, delivery and/or transplantation;

FIG. 2 is an enlarged view of a distal end segment of a typical injection cannula;

FIG. 3 is a cross-sectional view, taken along section lines 3-3 in FIG. 2, of the typical injection cannula;

FIG. 11 is a schematic diagram of an alternative illustrative embodiment of the systems for tissue removal, delivery and/or transplantation with a cannula instrument connected to a pump and a tissue-collecting container connected to the pump;

FIG. 12 is an enlarged view of a distal end segment of a typical aspiration cannula for the cannula instrument of FIG. 11;

DETAILED DESCRIPTION

Figure 4:
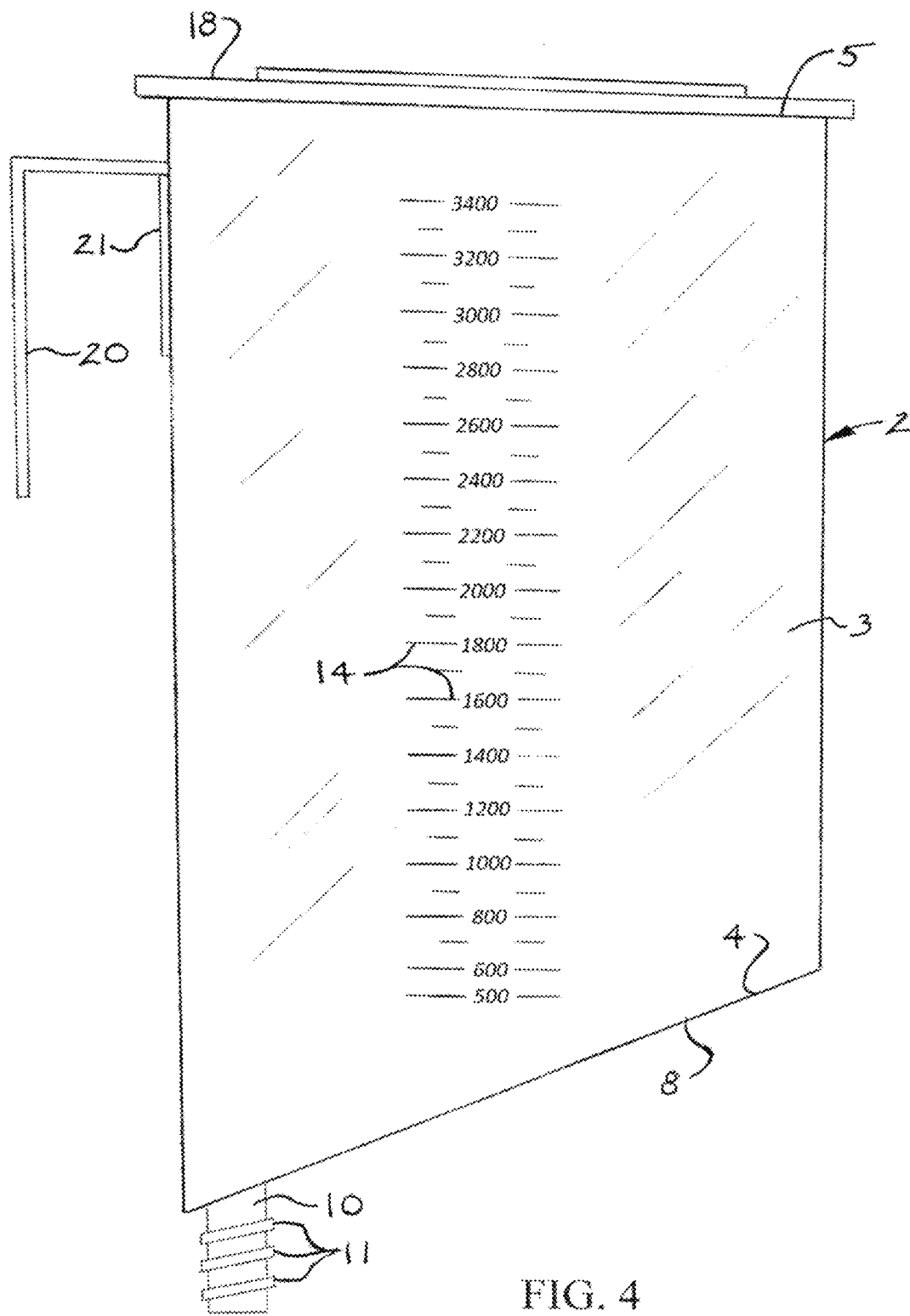
FIG. 4 is a side view of a typical dispensing canister according to some embodiments of the systems.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable users skilled in the art to practice the disclosure and are not intended to limit the scope of the claims. Moreover, the illustrative embodiments described herein are not exhaustive and embodiments or implementations other than those which are described herein and which fall within the scope of the appended claims are possible. Furthermore, there is no intention to be bound by any expressed or implied theory presented in the preceding technical field, background, brief summary or the following detailed description.

Referring initially to FIG. 1 of the drawings, an illustrative embodiment of the systems for tissue removal, delivery and/or transplantation, hereinafter system, is generally indicated by reference numeral 1. The system 1 may include at least one dispensing canister 2. A canister stand 24 may support the dispensing canister 2 for gravity-fed dispensing of material 42 such as tissue and/or fluid from the dispensing canister 2. A pump 44 may be disposed in fluid communication with the dispensing canister 2 through sterile pump tubing 46. A vibrational injection apparatus 50 may be disposed in fluid communication with the pump 44 through sterile apparatus tubing 48.

In exemplary application of the system 1, which will be hereinafter described, the dispensing canister 2 may contain a supply of material 42 which is to be injected into a recipient tissue underlying one or more anatomical sites on a patent (not illustrated) during a medical procedure. In some non-limiting applications, the material 42 may include a supply of crystalloid tumescent solution which is to be injected into the recipient tissue underlying one or more anatomical sites on the patient during a tumescent liposuction surgical procedure. In other non-limiting applications, the material 42 may include a supply of adipose tissue which is to be injected into the recipient tissue underlying one or more anatomical sites on the patient during an adipose tissue delivery or transplant surgical procedure. In still other non-limiting applications, the material 42 may include a soft-tissue filler such as hyaluronic acid and dispersion. In yet other non-limiting applications, the material 42 may include tissue regenerative cells such as adipose-derived stem cells (ASCs), pericytes and stem cells from bone marrow, for example and without limitation, in tissue transplantation procedures to regenerate damaged or deteriorated tissues in a patient. The pump 44 pumps the material 42 from the dispensing canister 2 to the vibrational injection apparatus 50. A surgeon or other medical personnel (not illustrated) operates and manipulates the vibrational injection apparatus 50, which vibrates as the material 42 is injected into the recipient tissue. The reciprocating or otherwise vibrating action of the vibrational injection apparatus 50 facilitates enhanced and uniform distribution of the material 42 throughout the recipient tissue, enabling the surgeon or medical personnel to achieve optimum results in the procedure. The vibrational injection apparatus 50 may include an injection cannula 60 having expanded tissue separation baskets 63. The expanded tissue separation baskets 63 of the injection cannula 60, in conjunction with the reduced areas 61 of the injection cannula 60 and the vibrating action of the vibrational injection apparatus 50, facilitates recipient tissue expansion and preparation for deposition of the material 42, further enhancing distribution and dispersion of the material 42 throughout the recipient tissues.

Referring next to FIG. 4 of the drawings, the dispensing canister 2 of the system 1 may include a canister wall 3 which may be generally cylindrical in shape. The canister wall 3 may have a canister wall bottom edge 4 and a canister wall top edge 5. A canister bottom panel 8 may be provided on the canister wall bottom edge 4 of the canister wall 3. The canister bottom panel 8 may have a beveled, sloped or slanted orientation. In some embodiments, the slope of the canister bottom panel 8 may vary from between about 5 degrees to about 150 degrees relative to the canister wall 3.

A dispensing spigot 10 may be disposed in fluid communication with the interior of the dispensing canister 2 at the lowest portion of the canister bottom panel 8 to facilitate connection of the pump tubing 46 (FIG. 1) to the dispensing canister 2. The dispensing spigot 10 may protrude downwardly from the canister bottom panel 8. The dispensing spigot 10 may include multiple spigot protrusions 11 which grip and secure the pump tubing 46 to the dispensing spigot 10. A removable canister lid 18 may be fitted on the canister wall top 5 of the canister wall 3. In some embodiments, the dispensing canister 2 may have a volume of about 1-5 L. Graduated canister markings 14 may be provided on the canister wall 3 to indicate the volumes of the dispensing canister 2. The dispensing canister 2 and its components may be fabricated of clear acrylic, plastic or ultra high molecular weight plastic, for example and without limitation, using conventional molding and/or other fabrication techniques known by those skilled in the art. The canister wall 3 may be transparent or clear to enable external visualization of the contents in the dispensing canister 2.

In some embodiments, a canister handle 20 may protrude from the exterior surface of the canister wall 3 for carrying and handling purposes. The canister handle 20 may be detachably attached to the canister wall 3 through a clip-on, slide-on or other suitable handle attachment mechanism 21, or may alternatively be fixed to the canister wall 3 according to the knowledge of those skilled in the art.

In some applications of the system 1, the sloped canister bottom panel 8 of the dispensing canister 2 may facilitate separation of a lower layer of crystalloid and blood from overlying adipose tissue in the material 42 which is to be injected into the recipient tissue in the patient. The dispensing spigot 10 and the pump tubing 46, 48 may have a diameter or width which is sufficient to facilitate transfer of adipose tissue in the material 42 without blockage to the pump 44 and the vibrational injection apparatus 50, respectively. In some non-limiting embodiments, the dispensing spigot 10 and the pump tubing 46, 48 may have a diameter of from about 3 mm to about 6 mm.

Figure 5:
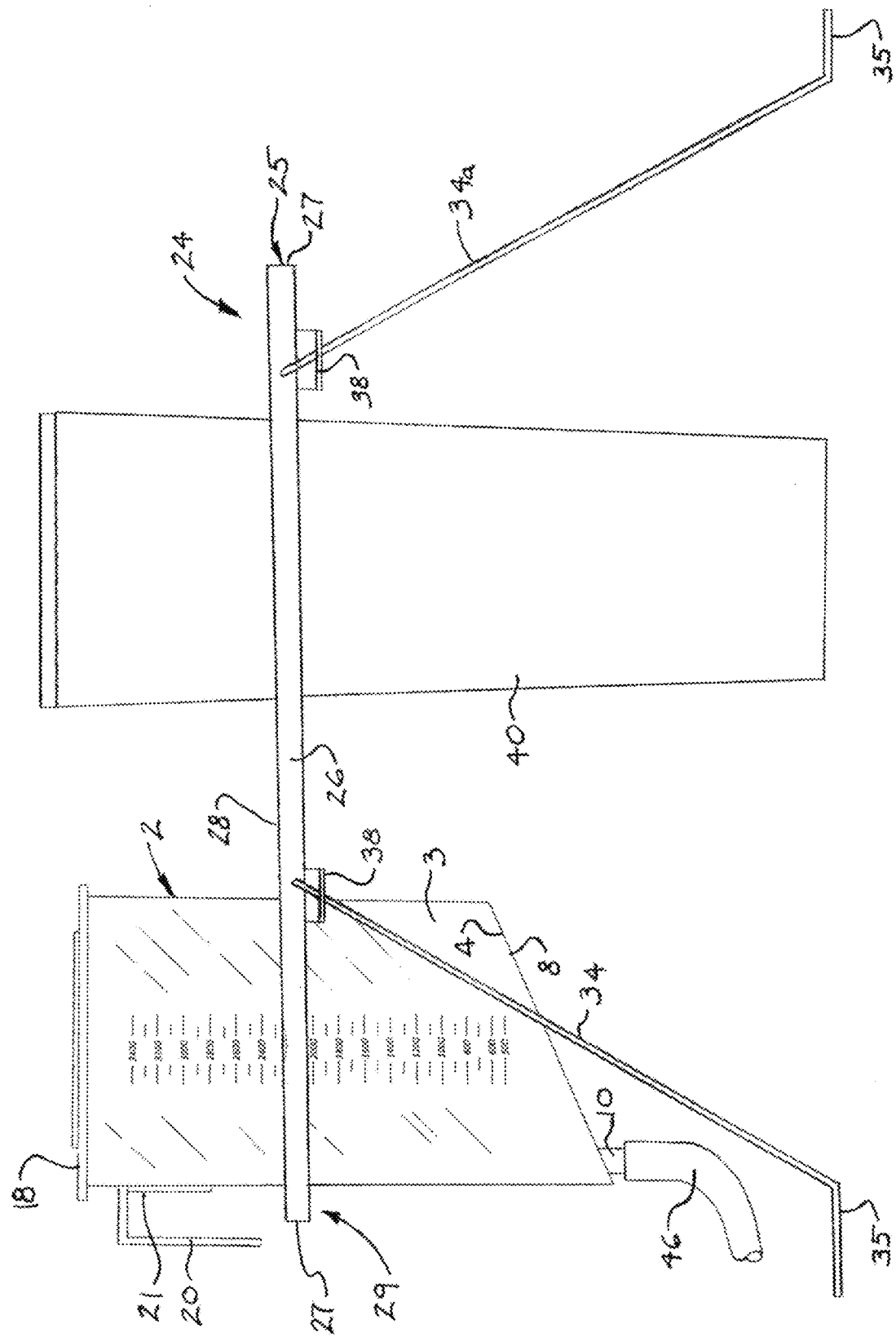
FIG. 5 is a side view of a typical canister stand according to some embodiments of the systems, with a dispensing canister and an accessory canister supported by the canister stand.
Figure 6:
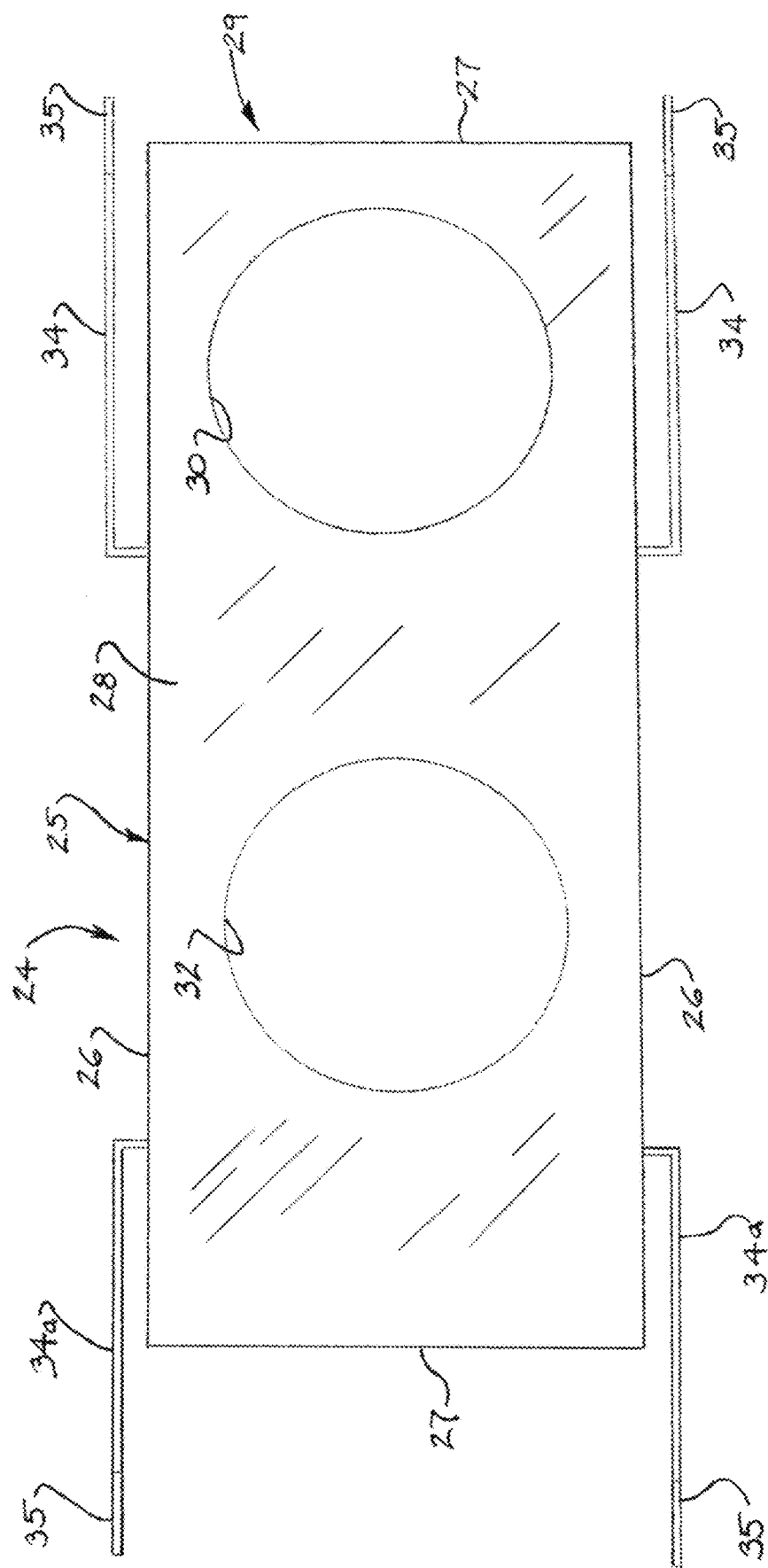
FIG. 6 is a top view of the typical canister stand with the dispensing canister and the accessory canister removed from the stand.

Referring next to FIGS. 5 and 6 of the drawings, the canister stand 24 of the system 1 may include a canister stand frame 25. In some embodiments, the canister stand frame 25 may be generally elongated and rectangular with a pair of side frame members 26 and a pair of end frame members 27 connecting the side frame members 26. A frame panel 28 may be supported by and extend between the side frame members 26 and the end frame members 27. As illustrated in FIG. 6, a first canister opening 30 and a second canister opening 32 may extend through the frame panel 28 in adjacent, spaced-apart relationship to each other.

A first set of parallel canister stand legs 34 may angle outwardly from the respective side frame members 26 beyond the end frame member 27 at a first end of the canister stand frame 25. Angled foot portions 35 may terminate the respective canister stand legs 34 to support the canister stand legs 34 on a table or other flat support surface (not illustrated). A second set of parallel canister stand legs 34a may angle outwardly from the respective side frame members 26 beyond the end frame member 27 at a second end of the canister stand frame 25. Angled foot portions 35 may terminate the respective canister stand legs 34a to support the canister stand legs 34a on the flat support surface (not illustrated). As illustrated in FIG. 5, each of the canister stand legs 34, 34a may extend through a leg opening (not illustrated) in a leg stabilizing bracket 38 which may extend outwardly from a corresponding side frame member 26 of the canister stand frame 25. The various components of the canister stand 24 may be fabricated of stainless steel and/or other metal alloy or nonmetallic material which is suitable for the purpose of stabilizing the dispensing canister 2 as well as any accessory canisters 40 (FIG. 5) during the medical procedure.

In some embodiments, at least one end of the canister stand frame 25 may protrude beyond at least the first set of canister stand legs 34 to form at least one overhang 29. The first canister opening 32 may extend through the overhang 29 of the canister stand frame 25. Throughout the medical procedure and during operation of the system 1, the dispensing canister 2 may remain seated in the first canister opening 30 at the overhang 29. The overhang 29 may facilitate gravity-fed flow of the material 42 directly from the dispensing container 2 through the dispensing spigot 10 into the pump tubing 46. The overhang 29 may also facilitate placement of a biohazard waste receptacle (not illustrated) directly beneath the dispensing container 2 upon subsequent conclusion of the medical procedure. Accordingly, residual waste material 42 (FIG. 1) which remains in the dispensing canister 2 can be selectively drained through the dispensing spigot 10 into the waste receptacle (not illustrated) and the residual waste material discarded.

The pump 44 (FIG. 1) of the system 1 may be any type of pump which is suitable for the purpose of pumping materials and fluids in surgical procedures. Such pumps may include but are not limited to roller pumps or peristaltic pumps which are well known by those skilled in the art. In some applications, the operational rate of the pump 44 may be programmable and the pump 44 may have the capability to pump the material 42 from the dispensing canister 2 to the vibrational injection apparatus 50 at a rate of from between about 10 cc per minute and about 500 cc per minute.

The vibrational injection apparatus 50 of the system 1 may be any type of hand-held motorized device which receives the material 42 from the pump 44 through the apparatus tubing 48 and vibrates while delivering the material 42 through an injection cannula 60 into a recipient tissue which underlies one or more of the anatomical sites on the patient (not illustrated) in a tissue removal, injection, transplantation or other medical procedure. A non-limiting example of a motorized vibrational injection apparatus 50 which is suitable for the purpose is described in U.S. Patent Application Publication No. US2013/0310749, which is incorporated by reference herein in its entirety. Other non-limiting examples of vibrational injection apparatuses which are suitable for the purpose will be hereinafter described. Accordingly, the vibrational injection apparatus 50 may include an apparatus handle 51. A vibration motor 52 may be provided in the apparatus handle 51. A cannula connector 53 may terminate the apparatus handle 51. The cannula connector 53 may facilitate coupling of the injection cannula 60 to the apparatus handle 51 such as through a luer lock connector or other suitable connection interface known by those skilled in the art. A power source connection 54 may extend from the apparatus handle 51 for connection to a suitable power source 58 such as through a power cord 59. A switch (not illustrated) may be provided on the apparatus handle 51 or on the power cord 59 to facilitate selective manual operation of the vibration motor 52. A tubing connector 55 may extend from the apparatus handle 51 for connection to the apparatus tubing 48 from the pump 44. In some embodiments, the vibrational injection apparatus 50 may impart a reciprocating motion 56 (FIG. 1) to the injection cannula 60. The reciprocating motion 56 may have an actuated amplitude of from about 1 mm to about 5 mm, for example and without limitation.

The injection cannula 60 may include an elongated cannula shaft 61 which has a shaft lumen 62 (FIG. 3) and terminates in a cannula tip 65. In some embodiments, the injection cannula 60 may be an exploded basket cannula having at least one tissue separation basket 63 provided on the cannula shaft 61 proximal to the cannula tip 65. In some embodiments, multiple tissue separation baskets 63 (such as 2-4 for example and without limitation) may be provided along the cannula shaft 61 in spaced-apart relationship to each other. Each tissue separation basket 63 may include multiple basket members 63a which may extend outwardly from the cannula shaft 61 in generally perpendicular relationship to each other. A cannula slot 63b (FIGS. 2 and 3) may extend through the wall of the cannula shaft 61 between each basket member 63a and the shaft lumen 62. The tissue separation baskets 63 may facilitate separation of and formation of multiple dispersion channels in the recipient tissue in the patient (not illustrated) for dispersion of the material 42 as the injection cannula 60 vibrates in the recipient tissue, as will be hereinafter further described. As illustrated in FIG. 1, in some embodiments, the injection cannula 60 incorporates a 5 to 20 degree angle placed in the long axis of the cannula 60, enhancing the vibrating or reciprocating action by providing an element of short axis reciprocation in addition to the long axis reciprocation, effectively enhancing the vibrational action of the device 50. In some embodiments, the injection cannula 60 may have a length of from about 20 cm to about 50 cm and the cannula shaft 61 may range in diameter from about 2 mm to about 5 mm. The injection cannula 60 may be fabricated of stainless steel, aluminum, ultra high molecular weight plastic and/or other disposable plastic or composite material. In some embodiments, the injection cannula 60 may have a length of about 2 cm to 20 cm and the canula shaft 61 may range in diameter from about 32 gauge to about 12 gauge (needle gauge).

In exemplary application, the system 1 facilitates injection of a material 42 such as a supply of crystalloid tumescent solution which is to be percutaneously or subcutaneously injected into a recipient tissue which underlies one or more anatomical sites on a patient during or preparatory to a tumescent liposuction surgical procedure or a supply of adipose tissue which is to be injected into the recipient tissue during an adipose tissue delivery or transplant surgical procedure. Accordingly, the material 42 may be placed in the dispensing container 2. The canister stand 24 may be placed on a table or other suitable support (not illustrated). The dispensing container 2 may be seated in the first canister opening 30 (FIG. 6) in the overhang 29 of the canister stand 24.

The pump tubing 46 may be connected, to the dispensing spigot 10 on the dispensing canister 2 and to the pump 44. The apparatus tubing 48 may be connected to the pump 44 and the tubing connector 55 on the vibrational injection apparatus 50. The vibrational injection apparatus 50 may be connected to the power source 58 through the power source connection 54.

An incision (not illustrated) is made at the anatomical site on the patient which overlies the recipient tissue into which the material 42 is to be injected. A surgeon (not illustrated) grips the apparatus handle 51 and inserts the injection cannula 60 into the incision. The vibration motor 52 may be operated to vibrate the injection cannula 60 typically according to the actuated amplitude of the reciprocating motion 56. As the pump 44 is operated to pump the material 42 from the dispensing canister 2 through the injection cannula 60 into the recipient tissue in the patient, the vibrating tissue separation baskets 63 on the injection cannula 60 may facilitate mechanical separation of connective tissue and create expanded dispersion channels in the recipient tissue which enhance diffusion of the material 42 throughout the tissue. The vibrating action of the injection cannula 60 may also facilitate egress of the material 42 from the injection cannula 60 into the recipient tissue. This effect may expedite removal of adipose tissue in all types of liposuction procedures including but not limited to percutaneous liposuction and liposuction directly into subcutaneous adipose tissue during liposuction and transplantation procedures.

In some applications, the system 1 may be implemented in tissue transplantation procedures to regenerate damaged or deteriorated tissues in a patient. Thus, the material 42 may include tissue regenerative cells such as adipose-derived stem cells (ASCs), pericytes and stem cells from bone marrow, for example and without limitation, which may initially be removed from donor tissue underlying one or more anatomical sites on the patient using conventional liposuction instruments and techniques. The material 42 which was removed from the donor tissue may subsequently be placed into the dispensing canister 2 and injected into the recipient tissue underlying one or more other anatomical sites on the patient using the vibrational injection apparatus 50 to infiltrate the recipient tissue or tissues and mediate release of soluble factors that stimulate adipogenesis and angiogenesis for rejuvenation treatment in the recipient tissue. The vibrating action of the injection cannula 60 may increase the quantity or proportion of the tissue regenerative cells which are subject to injury before and as they enter the recipient tissue. The injured tissue regenerative cells may release soluble factors which recruit and activate other tissue regenerative cells and bone-marrow derived stem cells in the recipient tissue. The released factors may promote angiogenesis and adipogenesis, filling and restoring the original appearance of the anatomical site which overlies the recipient tissue. This procedure may be carried out as described in co-pending U.S. application Ser. No. 14/173,021, filed Feb. 5, 2014 and entitled TISSUE REJUVENATION METHODS AND TISSUE TRANSFER DEVICES SUITABLE FOR IMPLEMENTATION THEREOF, which application is incorporated by reference herein in its entirety.

Upon conclusion of the injection procedure, the vibration motor 52 may be turned off and the injection cannula 60 removed from the recipient tissue in the patient. Any residual material 42 which remains in the dispensing canister 2 may be drained through the dispensing spigot 10 into a biohazard waste receptacle (not illustrated) which is placed directly beneath the dispensing canister 2 after detachment of the pump tubing 46. Alternatively, the residual material 42 may be decanted from the dispensing canister 2 by gripping the canister handle 20 and pouring the residual material 42 into the waste receptacle.

Figure 7:
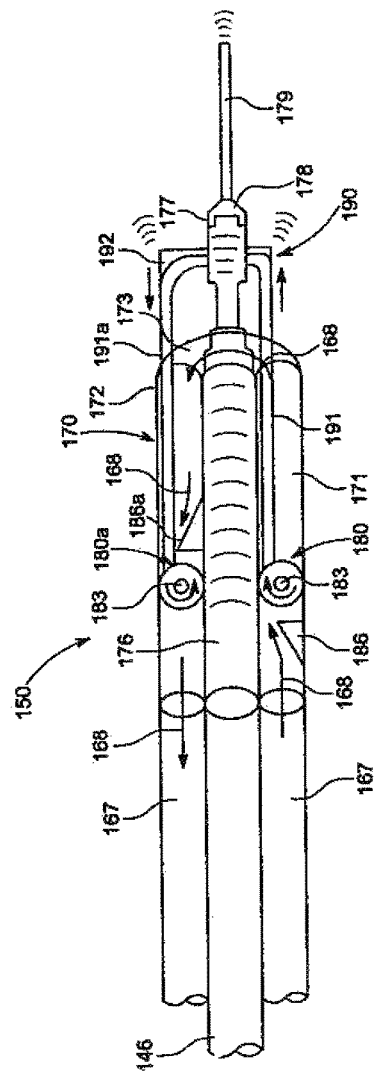
FIG. 7 is a side view of a typical pneumatic vibrational injection apparatus according to some embodiments of the systems.

Referring next to FIGS. 7-10A of the drawings, an alternative illustrative embodiment of the systems 101 (FIG. 10A) which utilizes a pneumatic vibrational injection apparatus 150 is illustrated. The pneumatic vibrational injection apparatus 150 may include an apparatus housing 170. As illustrated in FIG. 7, the apparatus housing 170 may include an air inlet chamber 171, an air outlet chamber 172 and a connecting chamber 173 which connects the air outlet chamber 172 to the air inlet chamber 171. As further illustrated in FIG. 7, in operation of the apparatus 150, which will be hereinafter described, air 168 flows through the air inlet chamber 171, the connecting chamber 173 and the air outlet chamber 172, respectively, of the apparatus housing 170 for purposes which will be hereinafter described.

Figure 10:
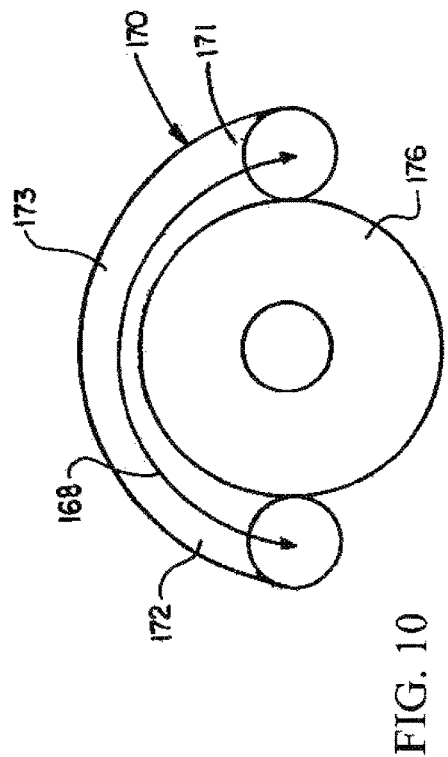
FIG. 10 is a cross-sectional view illustrating an air inlet chamber, an air outlet chamber and a connecting chamber bypassing an injection chamber in the pneumatic vibrational injection apparatus according to some embodiments of the systems.

An injection chamber 176 may be disposed between the air inlet, chamber 171 and the air outlet chamber 172. As illustrated in FIG. 10, the injection chamber 176 may bypass the connecting chamber 173 at a forward end of the apparatus housing 170. An injection nozzle 177 may be disposed in fluid communication with the injection chamber 176. The injection nozzle 177 may extend from the forward end of the apparatus housing 170. An injection cannula 179 may be coupled to the injection nozzle 177 through a suitable needle connector 178 such as a luer-lock connector, for example and without limitation.

Figure 9:
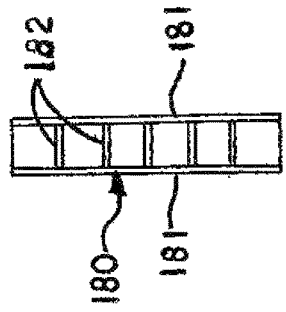
FIG. 9 is an edge view of the typical transducer wheel.
Figure 8:
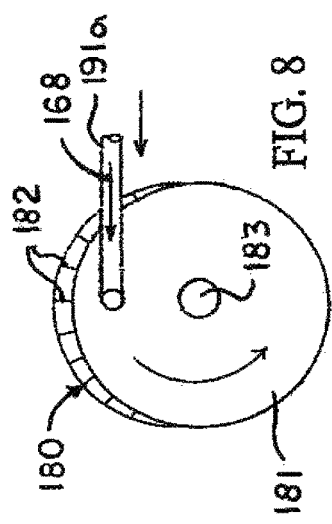
FIG. 8 is a perspective view of a typical air-actuated transducer wheel of a pneumatic vibrational injection apparatus according to some embodiments of the systems.

An inlet transducer wheel 180 and an outlet transducer wheel 180a may be mounted for rotation in the air inlet chamber 171 and the air outlet chamber 172, respectively, of the apparatus housing 170 such as via respective wheel axles 183. As illustrated in FIG. 9, each of the inlet transducer wheel 180 and the outlet transducer wheel 180a may include a pair of spaced-apart transducer wheel disks 181. Multiple transducer wheel blades 182 may extend in radial orientation from the wheel axle 183 outwardly between the transducer wheel disks 181 in spaced-apart relationship to each other and around the circumference of the corresponding inlet transducer wheel 180 and outlet transducer wheel 180a.

As illustrated in FIG. 7, an inlet air flow director 186 may be provided in the air inlet chamber 171 of the apparatus housing 170, upstream of the inlet transducer wheel 180 relative to the direction of the flow of air 168 through the apparatus housing 170. The inlet air flow director 186 may direct the air 168 which flows through the air inlet chamber 171 against the transducer wheel blades 182 of the inlet transducer wheel 180 such that the inlet transducer wheel 180 rotates in a first direction, such as the clockwise direction in the non-limiting example illustrated in FIG. 7. An outlet air flow director 186a may likewise be provided in the air outlet chamber 172 upstream of the outlet transducer wheel 180a. The outlet air flow director 186a may direct the air 168 which flows through the air outlet chamber 172 against the transducer wheel blades 182 of the outlet transducer wheel 180a such that the outlet transducer wheel 180a rotates in a second direction, such as the counterclockwise direction in the non-limiting example illustrated in FIG. 7.

A vibration transducer 190 may be disposed in physical contact with the inlet transducer wheel 180 and the outlet transducer wheel 180a. The injection nozzle 177 may be disposed in physical contact with the vibration transducer 190. In some embodiments, the vibration transducer 190 may include an inlet transducer arm 191 which extends from the inlet transducer wheel 180 and an outlet transducer arm 191a which extends from the outlet transducer wheel 180a. A transducer bridge 192 may extend between the inlet transducer arm 191 and the outlet transducer arm 191a. The injection nozzle 177 may extend through a nozzle opening (not illustrated) in the transducer bridge 192. Accordingly, responsive to flow of air 168 through the air inlet chamber 171, the connecting chamber 173 and the air outlet chamber 172, respectively, the inlet transducer wheel 180 may rotate in the first direction to apply a pushing motion to the inlet transducer arm 191. Conversely, the outlet transducer wheel 180a may rotate in the second direction to simultaneously apply a pulling, motion to the outlet transducer arm 191a.

This simultaneous antagonistic pushing and pulling action on the inlet transducer arm 191 and the outlet transducer arm 191a, respectively, imparts vibration to the vibration transducer 190, which in turn imparts vibration to the injection nozzle 177 and the injection cannula 179.

Figure 10A:
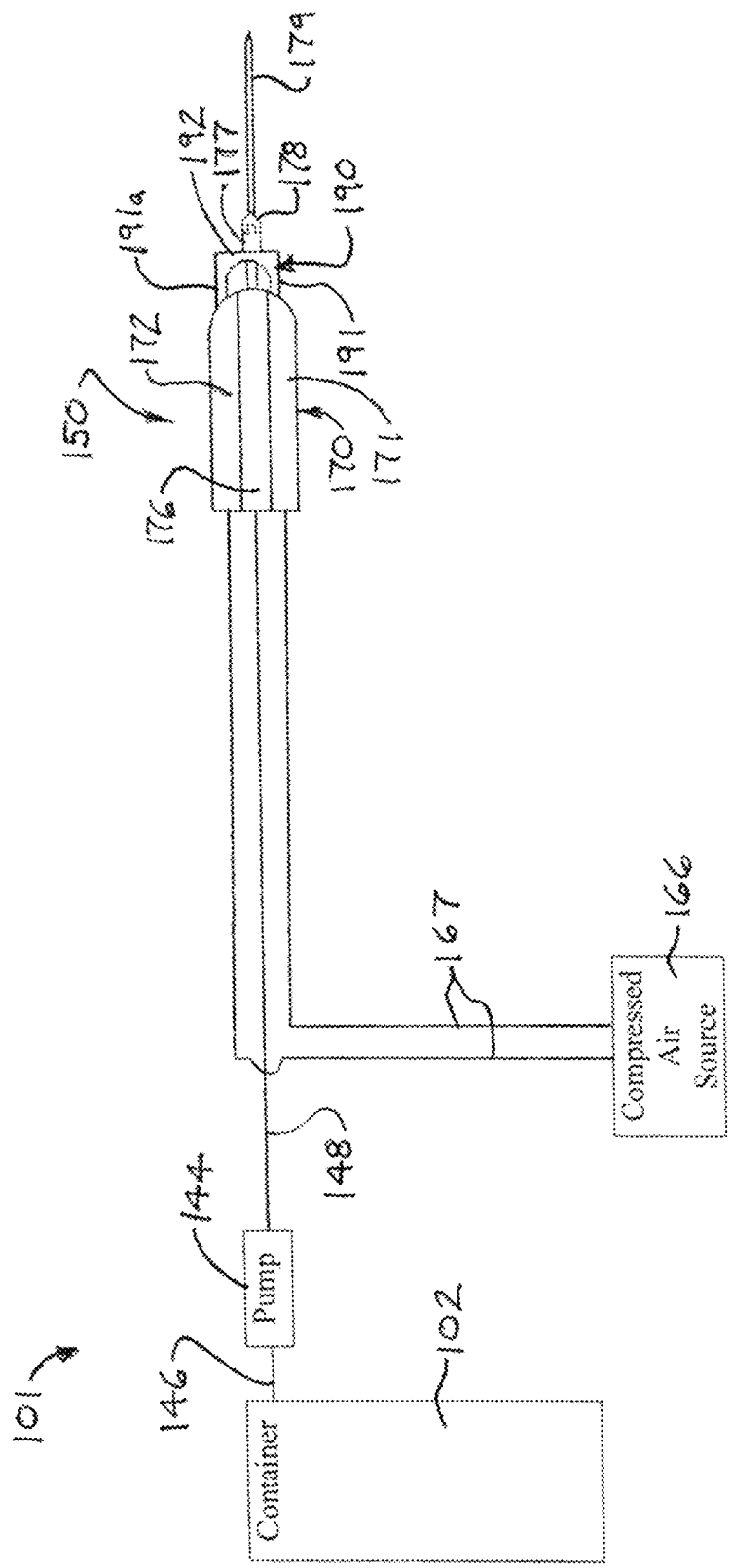
FIG. 10A is a schematic block diagram of an illustrative embodiment of the systems for tissue removal, delivery and/or transplantation which utilizes a pneumatic vibrational injection apparatus.

As illustrated in FIG. 10A, a compressed air source 166 may be disposed in pneumatic communication with the air inlet chamber 171 and the air outlet chamber 172, respectively, of the apparatus housing 170 through a pair of compressed air lines 167. The compressed air lines 167 may be detachably coupled to the respective air inlet chamber 171 and the air outlet chamber 172 through any type of airtight hose coupling which is known by those skilled in the art and suitable for the purpose. A pump 144, such as the peristaltic pump 44 which was heretofore described with respect to FIG. 1, for example and without limitation, may be disposed in fluid communication with the injection chamber 176 of the apparatus housing 170 through apparatus tubing 148. A dispensing canister 102, such as the dispensing canister 2 which was heretofore described with respect to FIG. 4, may be disposed in fluid communication with the pump 144 through pump tubing 146.

Operation of the pneumatic vibrational injection apparatus 150 of the system 101 may be as was heretofore described with respect to operation of the motorized vibrational apparatus 50 of the system 1 in FIG. 1. As illustrated in FIG. 7, the flow of air 168 through the air inlet chamber 171, the connecting chamber 173 and the air outlet chamber 172, respectively, imparts vibration to the injection cannula 179 through the vibration transducer 170 as was heretofore described.

Figure 10B:
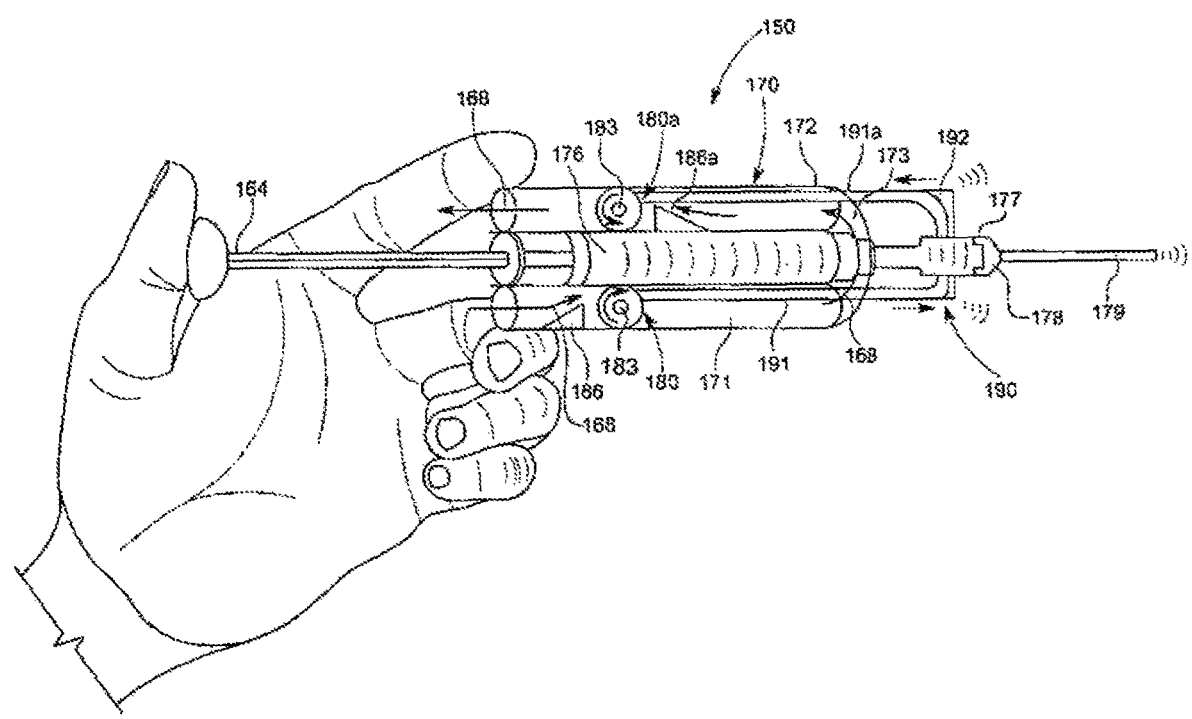
FIG. 10B is a side view of a typical hand-actuated pneumatic vibrational injection apparatus according to some embodiments of the systems.

Referring next to FIG. 10B of the drawings, a typical alternative, hand-actuated pneumatic vibrational injection apparatus 150a which may be used in implementation of system 101 in FIG. 10A is illustrated. In the hand-operated pneumatic vibrational injection apparatus 150a, a syringe plunger 164 may slidably engage the injection chamber 176 in the apparatus housing 170 instead of the pump 144 being disposed in fluid communication with the injection chamber 176 as was heretofore described with respect to the system 101 illustrated in FIG. 10A. Accordingly, the material 42 (FIG. 1) which is injected into the recipient tissue in the patient may first be drawn into the injection chamber 176 through the injection cannula 179 by drawing a vacuum on the injection chamber 176 through rearward displacement of the syringe plunger 164. The material 42 may be expelled from the injection chamber 176 through the injection cannula 179 into the recipient tissue by subsequently generating positive pressure in the injection chamber 176 through forward displacement of the syringe plunger 164. Simultaneously, air 168 may be distributed through the air inlet chamber 171, the connecting chamber 173 and the air outlet chamber 172, respectively, of the apparatus housing 170, typically through the compressed, air lines 167 coupled to the compressed air source 166 (FIG. 10A), to impart vibration to the injection cannula 179 as was heretofore described with respect to operation of the vibrational injection apparatus 150 in FIG. 7.

Referring next to FIGS. 11-14 of the drawings, an alternative illustrative embodiment of a system 201 with a cannula instrument 294 connected to a pump 244 and a tissue-collecting container 202 is illustrated. The cannula instrument 294 may include a lightweight cannula handle 295. An aspiration cannula 400 may extend from the cannula handle 295. In some embodiments, the aspiration cannula 400 may have a length of from about 30 cm to about 50 cm and a diameter of from about 3 mm to about 5 mm. As illustrated in FIG. 12, the aspiration cannula 400 may include a series of staggered cannula openings 401 proximal to the cannula tip 402. Each of the cannula openings 401 may have a circular, elliptical or other shape. In some embodiments, the aspiration cannula 400 may include about 10-14 cannula openings 401. The aspiration cannula 400 may be stainless steel, aluminum, clear plastic such as ultrahigh molecular weight plastic and/or other suitable material.

Figure 14:
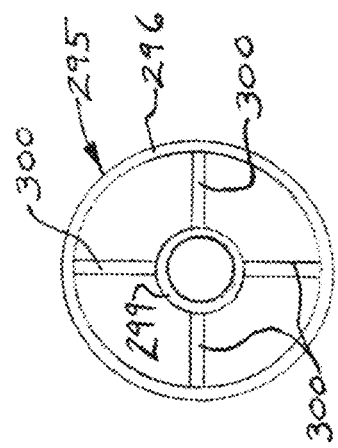
FIG. 14 is a front view of the typical handle for the cannula instrument of FIG. 11.
Figure 13:
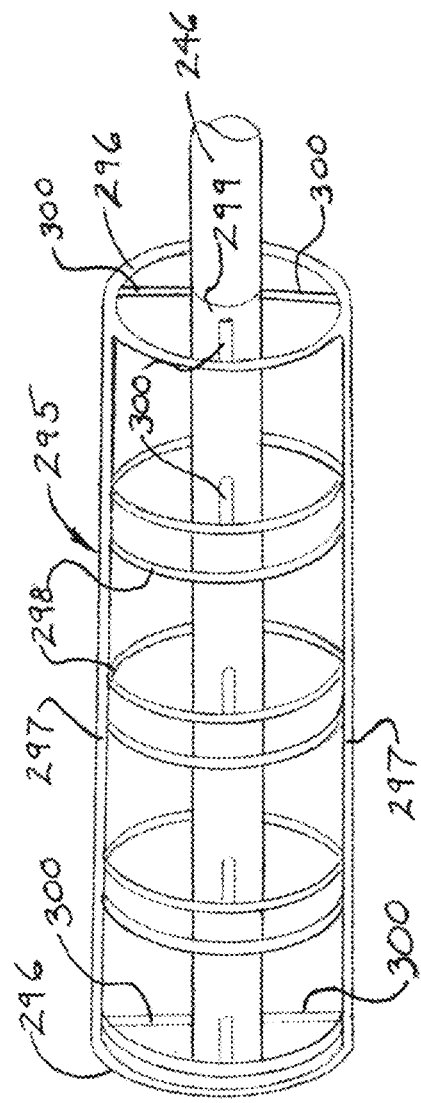
FIG. 13 is a perspective view of a typical handle for the cannula instrument of FIG. 11.

As illustrated in FIGS. 13 and 14, the cannula handle 295 of the cannula instrument 294 may have a fenestrated or caged design with a pair of spaced-apart handle end frame members 296. Multiple elongated handle side frame members 297 may extend between the handle end frame members 296 in parallel, spaced-apart relationship to each other along the length of the cannula handle 295. Multiple handle middle frame members 298 may extend between the handle side frame members 297 in spaced-apart relationship to each other between the handle end frame members 296. An elongated tubing receptacle 299 may extend through and in generally concentric relationship to the handle end frame members 296 and the handle middle frame members 298. Connecting frame members 300 may extend between the tubing receptacle 299 and the handle end frame members 296 and between the tubing receptacle 299 and one or more of the handle middle frame members 298 to minimize structure and material which connects the pump tubing 246 to the cannula handle 295. The cannula handle 295 may include lightweight aluminum, steel and/or other metal alloy and/or plastic or other suitable lightweight rigid material.

As illustrated in FIG. 11, in exemplary application, the aspiration cannula 400 may be connected to the cannula handle 295 via a luer lock or other suitable cannula connector 404. Apparatus tubing 248 may connect a pump 244 to the aspiration cannula 400 through the cannula connector 404. Pump tubing 246 may connect the pump 244 to a container 202. The apparatus tubing 248 may extend through the tubing receptacle 299 centralized along the length of the cannula handle 295. Accordingly, during a liposuction or other medical procedure, a surgeon (not illustrated) grips the cannula handle 295 and inserts the aspiration cannula 400 through an incision (not illustrated) into recipient tissue which underlies at one or more anatomical sites on a patient. The pump 244 may be operated to suction adipose tissue from the patient through the aspiration cannula 400, the apparatus tubing 248 and the pump tubing 246, respectively, into the container 202. The surgeon may repeatedly move the aspiration cannula 400 back and forth in multiple strokes to ensure that adipose tissue is adequately and uniformly removed from the desired anatomical area of the patient. It will be appreciated by those skilled in the art that the lightweight construction of the cannula handle 295 reduces the work which the surgeon is required to exert with each stroke of the aspiration cannula 400 within the anatomical area of the patient which is being shaped. Accordingly, the lightweight cannula handle 295 prevents the surgeon from becoming fatigued, particularly in liposuction procedures in which large quantities of adipose tissue are removed from the patient.

Figure 15:
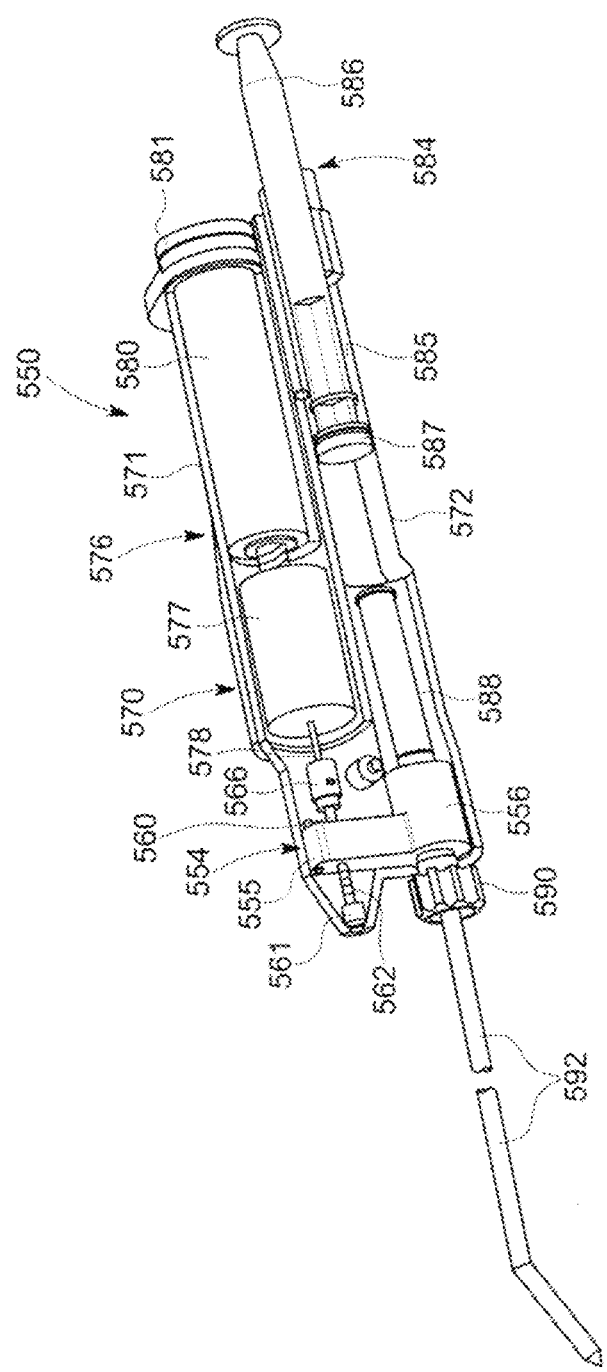
FIG. 15 is a sectional perspective view of a typical handheld vibrational injection apparatus according to some embodiments of the systems.

Referring next to FIG. 15 of the drawings, another typical handheld vibrational injection apparatus 550 according to some embodiments of the systems is illustrated. The vibrational injection apparatus 550 may include an apparatus housing 570 which may be generally elongated. The apparatus housing 570 may include a vibration mechanism compartment 571 and an adjacent injector compartment 572. A vibration mechanism 576 may be provided in the vibration mechanism compartment 571 and a material injector 584 may be provided in the injector compartment 572 of the apparatus housing 570.

The vibration mechanism 576 may include any type of mechanical, pneumatic or other device which is capable of imparting vibration to the material injector 584 typically in a manner which will be hereinafter described. In some embodiments, the vibration mechanism 576 may include the pneumatic vibrating mechanism which was heretofore described with respect to the vibrational injection apparatuses 150, 150*a* in FIGS. 7-10B. In other embodiments, the vibration mechanism 576 may include a vibration mechanism motor 577. A battery compartment 580 may be provided in the vibration mechanism compartment 571 adjacent to the vibration mechanism motor 577. The battery compartment 580 may be electrically connected to the vibration mechanism motor 577 and may contain at least one battery (not illustrated) which supplies electrical current for operation of the vibration mechanism motor 577. The vibration mechanism motor 577 may drivingly engage a vibration shaft 578 for reciprocation of the vibration shaft 578 according to the knowledge of those skilled in the art. An injector vibrating shaft 560 may be engaged for reciprocation by the vibration shaft 578. A shaft connector 566 may couple the injector vibrating shaft 560 to the vibration shaft 578.

The material injector 584 may include any type of mechanism, structure or device which is suitable for the purpose of receiving or containing a material 42 (FIG. 1) and facilitating injection of the material into the patient or removing the material 42 from the patient. The material injector 584 may include at least one injection chamber 585. In some embodiments, a hand-operated or automated plunger 586 may terminate in a plunger head 587 which slides within the injection chamber 585 to facilitate selective drawing of the material 42 into or expulsion of the material 42 from the injection chamber 585. In other embodiments, a pump 44 (FIG. 1) may be connected in fluid communication with the injection chamber 585 through apparatus tubing 48. A dispensing canister 2 may be connected in fluid communication with the pump 44 and may contain the material 42 which is to be injected into the patient.

A telescoping injector tube 588 in the injector compartment 572 of the apparatus housing 570 may be disposed in fluid communication with the injection chamber 585. A cannula connector 590 may be disposed in fluid communication with the injector tube 588 on the exterior of the apparatus housing 570. The cannula connector 590 may facilitate coupling of an injection cannula 592 to the material injector 584 such as through a luer lock connector or other suitable connection interface known by those skilled in the art. In some embodiments, the injection cannula 592 may have a length of from about 2 cm to about 20 cm and the cannula shaft of the injection cannula 592 may range in diameter from about 32 gauge to about 12 gauge (needle gauge).

A driver 554 may couple the injector vibrating shaft 560 of the vibration mechanism 576 to the injector tube 588 of the material injector 584. The driver 554 may include a generally elongated driver bridge 555 and, a driver head 556 which terminates the driver bridge 555. The reciprocating vibration shaft 560 may extend through a shaft opening (not illustrated) in the driver bridge 555 and may engage the driver bridge 555 for reciprocation of the driver 554 with the reciprocating vibration shaft 560. The injector tube 588 may communicate with a tube opening (not illustrated) in the driver head 556 and may extend and retract in a telescoping motion with the reciprocating driver 554. A spring stop 561 may terminate the vibration shaft 560. A driver return spring 562 may be interposed between the driver bridge 555 and the spring stop 561. Accordingly, in operation of the vibrational injection apparatus 550, the vibration motor 577 repeatedly reciprocates the reciprocating vibration shaft 578 and the injector vibrating shaft 560 between retracted and extended positions. The driver bridge 555 and the driver head 556 of the driver 554 reciprocate with the injector vibrating shaft 560. Thus, the driver head 556 of the driver 554 reciprocates the telescoping injector tube 588, which telescopes and vibrates the material 42 as it flows from the injector chamber 585 through the injector tube 588 and the injection cannula 592 coupled to the cannula connector 590 and is discharged from the injection cannula 592 into the patient (not illustrated).

Application of the vibrational injection apparatus 550 may be as was heretofore described with respect to the vibrational injection apparatus 50 in the system 1 illustrated in FIG. 1. Accordingly, material 42 may be drawn into the injection chamber 585 of the material injector 584 through the injection cannula 592 by actuation of the plunger 586. The material 42 may include a supply of crystalloid tumescent solution which is to be percutaneously or subcutaneously injected into a recipient tissue which underlies one or more anatomical sites on a patient during or preparatory to a tumescent liposuction surgical procedure or a supply of adipose tissue which is to be injected into the recipient tissue during an adipose tissue delivery or transplant surgical procedure. Alternatively, the material 42 may include a soft-tissue filler such as hyaluronic acid and dispersion which is to be injected in a patient in body shaping procedures. Still further in the alternative, the material 42 may include tissue regenerative cells such as adipose-derived stem cells (ASCs), pericytes and stem cells from bone marrow, for example and without limitation, in tissue transplantation procedures to regenerate damaged or deteriorated tissues in a patient.

The vibration mechanism motor 577 may be operated to vibrate the telescoping injector tube 588 of the material injector 584 through the reciprocating the vibration shaft 578, the injector vibrating shaft 560 and the driver 554 as the injector 584 is operated to expel the material 42 from the injection chamber 585 through the injector tube 588, the driver head 556 and the cannula connector 590 and into the injection cannula 592, respectively. As the material 42 is discharged from the injection cannula 592 into the patient, the vibrating motion of the injector tube 588 is transmitted to the injector cannula 592 through the driver head 556 and the cannula connector 590. The vibrating injection cannula 592 may facilitate mechanical separation of connective tissue and create expanded dispersion channels in the recipient tissue which enhance diffusion of the material 42 throughout the tissue, facilitate egress of the material 42 from the injection cannula 592 into the recipient tissue and/or increase the quantity or proportion of tissue regenerative cells which are in the material 42 and subject to injury before and as they enter the recipient tissue. Thus, the injured tissue regenerative cells may release soluble factors which recruit and activate other tissue regenerative cells and bone-marrow derived stem cells in the recipient tissue. The released factors may promote angiogenesis and adipogenesis, filling and restoring the original appearance of the anatomical site which overlies the recipient tissue.

While illustrative embodiments of the disclosure have been described above, it will be recognized and understood that various modifications can be made in the disclosure and the appended claims are intended to cover all such modifications which may fall within the spirit and scope of the disclosure.

What is claimed is:

1. A canister stand suitable for holding at least one dispensing canister, comprising:
   a canister stand frame having a first end and a second end;
   a frame panel carried by the canister stand frame;
   a first set of canister stand legs extending from the canister stand frame at a first set of leg attachment points;
   a second set of canister stand legs extending from the canister stand frame at a second set of leg attachment points;
   at least one overhang formed by the canister stand frame, the at least one overhang extending from the first set of leg attachment points to the first end of the canister stand frame; and
   at least one canister opening in the frame panel at the at least one overhang, the at least one canister opening having a width or diameter confined between the first set of leg attachment points and the first end of the canister stand frame, the at least one canister opening suitably sized and configured to accommodate the at least one dispensing canister.

2. The canister stand of claim 1 wherein the canister stand frame comprises a pair of side frame members, a pair of first and second end frame members connecting the pair of side frame members, and the first set of canister stand legs angle outwardly from the pair of side frame members, respectively, at the first end frame member of the canister stand frame and the second set of canister stand legs angle outwardly from the pair of side frame members, respectively, at the second end frame member of the canister stand frame.

3. The canister stand of claim 2 further comprising angled foot portions terminating the first set of canister stand legs and the second set of canister stand legs, respectively, the angled foot portions configured to support the first set of canister stand legs and the second set of canister stand legs on a flat support surface.

4. The canister stand of claim 2 wherein the first set of canister stand legs comprises a first set of parallel canister stand legs angling outwardly from the pair of side frame members, respectively, beyond the first end frame member at the first end of the canister stand frame and the second set of canister stand legs comprises a second set of parallel canister stand legs angling outwardly from the pair of side frame members, respectively, beyond the second end frame member at the second end of the canister stand frame.

5. The canister stand of claim 2 further comprising a plurality of leg stabilizing brackets extending outwardly from each corresponding one of the pair of side frame members of the canister stand frame, and wherein each of the first set of canister stand legs and the second set of canister stand legs extends through a corresponding one of the plurality of leg stabilizing brackets.

6. The canister stand of claim 2 wherein the at least one canister opening comprises a first canister opening extending through the frame panel at the at least one overhang and a second canister opening extending through the frame panel in adjacent, spaced-apart relationship to the first canister opening.

7. The canister stand of claim 1 wherein the canister stand frame is generally elongated and rectangular.

8. The canister stand of claim 1 further comprising at least one dispensing canister configured to be seated in the at least one canister opening for gravity-fed dispensing of material from the at least one dispensing canister.

9. A canister stand, comprising:
   a canister stand frame having a first end and a second end;
   a frame panel carried by the canister stand frame;
   a first set of canister stand legs extending from the canister stand frame at a first set of leg attachment points;
   a second set of canister stand legs extending from the canister stand frame at a second set of leg attachment points;
   at least one overhang formed by the canister stand frame, the at least one overhang extending from the first set of leg attachment points to the first end of the canister stand frame;
   at least one canister opening in the frame panel at the at least one overhang, the at least one canister opening having a width or diameter confined between the first set of leg attachment points and the first end of the canister stand frame; and
   at least one dispensing canister configured to be seated in the at least one canister opening, the at least one dispensing canister including:
      a canister wall having a canister wall bottom edge and a canister wall top edge;
      a canister bottom panel on the canister wall bottom edge of the canister wall, the canister bottom panel having a beveled, sloped or slanted orientation; and
      at least one dispensing spigot disposed in fluid communication with the dispensing canister at a lowest portion of the canister bottom panel.

10. The canister stand of claim 9 wherein the canister stand frame comprises a pair of side frame members, a pair of first and second end frame members connecting the pair of side frame members, and the first set of canister stand legs angle outwardly from the pair of side frame members, respectively, at the first end frame member of the canister stand frame and the second set of canister stand legs angle outwardly from the pair of side frame members, respectively, at the second end frame member of the canister stand frame.

11. The canister stand of claim 10 further comprising angled foot portions terminating the first set of canister stand legs and the second set of canister stand legs, respectively, the angled foot portions configured to support the first set of canister stand legs and the second set of canister stand legs on a flat support surface.

12. The canister stand of claim 10 wherein the first set of canister stand legs comprises a first set of parallel canister stand legs angling outwardly from the pair of side frame members, respectively, beyond the first end frame member at the first end of the canister stand frame and the second set of canister stand legs comprises a second set of parallel canister stand legs angling outwardly from the pair of side frame members, respectively, beyond the second end frame member at the second end of the canister stand frame.

13. The canister stand of claim 10 further comprising a plurality of leg stabilizing brackets extending outwardly from each corresponding one of the pair of side frame members of the canister stand frame, and wherein each of the first set of canister stand legs and the second set of canister stand legs extends through a corresponding one of the plurality of leg stabilizing brackets.

14. The canister stand of claim 10 wherein the at least one canister opening comprises a first canister opening extending through the frame panel at the at least one overhang and a second canister opening extending through the frame panel in adjacent, spaced-apart relationship to the first canister opening.

15. The canister stand of claim 14 further comprising an accessory canister seated in the second canister opening.

16. The canister stand of claim 9 wherein the canister stand frame is generally elongated and rectangular.

17. A canister stand suitable for holding a dispensing canister, comprising:
   an elongated, rectangular canister stand frame including:
      a pair of side frame members;
      a pair of end frame members connecting the pair of side frame members at first and second ends, respectively, of the canister stand frame;
      a first set of parallel canister stand legs angling outwardly from the pair of side frame members, respectively, at a first set of leg attachment points;
      a second set of parallel canister stand legs angling outwardly from the pair of side frame members, respectively, at a second set of leg attachment points;
      angled foot portions terminating the first set of canister stand legs and the second set of canister stand legs, respectively, the angled foot portions configured to support the first set of canister stand legs and the second set of canister stand legs on a flat support surface;
      an overhang formed by the first end of the canister stand frame protruding beyond the first set of parallel canister stand legs, the overhang extending from the first set of leg attachment points to the first end of the canister stand frame;
      a frame panel carried by the canister stand frame;
      a first canister opening extending through the frame panel at the overhang, the first canister opening having a width or diameter confined between the first set of leg attachment points and the first end of the canister stand frame; and
      a second canister opening extending through the frame panel in adjacent, spaced-apart relationship to the first canister opening; and
   a dispensing canister configured to be seated in the first canister opening, the dispensing canister including:
      a canister wall having a canister wall bottom edge and a canister wall top edge;
      a canister bottom panel on the canister wall bottom edge of the canister wall, the canister bottom panel having a beveled, sloped or slanted orientation; and
      at least one dispensing spigot disposed in fluid communication with the dispensing canister at a lowest portion of the canister bottom panel.

18. The canister stand of claim 17 further comprising an accessory canister configured to be seated in the second canister opening.

19. The canister stand of claim 17 further comprising a plurality of leg stabilizing brackets extending outwardly from each corresponding one of the pair of side frame members of the canister stand frame, and wherein each of the first set of parallel canister stand legs and the second set of parallel canister stand legs extends through a corresponding one of the plurality of leg stabilizing brackets.

20. The canister stand of claim 17 further comprising a pump disposed in fluid communication with the at least one dispensing spigot on the dispensing canister and a vibrational injection apparatus disposed in fluid communication with the pump.

* * * * *